US007404943B2

(12) United States Patent
Eckert et al.

(10) Patent No.: US 7,404,943 B2
(45) Date of Patent: Jul. 29, 2008

(54) METHODS FOR SOLUBILIZING AND RECOVERING FLUORINATED COMPOUNDS

(75) Inventors: Charles A. Eckert, Atlanta, GA (US); Philip G. Jessop, Kingston (CA); Charles L. Liotta, Atlanta, GA (US)

(73) Assignees: The Regents of the University of California, Oakland, CA (US); Georgia Tech Research Corporation, Atlanta, GA (US)

( * ) Notice: Subject to any disclaimer, the term of this patent is extended or adjusted under 35 U.S.C. 154(b) by 924 days.

(21) Appl. No.: 10/479,436

(22) PCT Filed: May 30, 2002

(86) PCT No.: PCT/US02/17110

§ 371 (c)(1),
(2), (4) Date: Jul. 22, 2004

(87) PCT Pub. No.: WO02/096550

PCT Pub. Date: Dec. 5, 2002

(65) Prior Publication Data

US 2005/0015936 A1 Jan. 27, 2005

Related U.S. Application Data

(60) Provisional application No. 60/294,909, filed on May 30, 2001.

(51) Int. Cl.
*C01B 9/08* (2006.01)
(52) U.S. Cl. ....................................... 423/489; 423/490
(58) Field of Classification Search ................... 23/295, 23/295 R, 300; 423/464, 489, 490, 606
See application file for complete search history.

(56) References Cited

U.S. PATENT DOCUMENTS

| 4,512,846 | A | 4/1985 | Shlichta |
| 5,777,121 | A | 7/1998 | Curran et al. |
| 5,859,247 | A | 1/1999 | Curran et al. |
| 5,864,923 | A | 2/1999 | Rouanet et al. |
| 6,156,896 | A | 12/2000 | Curran et al. |
| 6,372,906 | B1 | 4/2002 | Curran et al. |
| 6,376,676 | B1 | 4/2002 | Curran et al. |

FOREIGN PATENT DOCUMENTS

| WO | WO 98/00376 | 1/1998 |
| WO | WO 00/33956 | 6/2000 |

OTHER PUBLICATIONS

Anonymous (1999). "Fluorous Biphasic Catalysis With Metal-Centred Catalysts." *Green Chemistry* 1(2): G45.
Barrett, A. G. M. et al. (2000). "Fluorous Biphase Catalytic Friedel-Crafts Acylation: Ytterbium Tris(Perfluoroalkanesulfonyl)Methide Catalysts." *Synlett* (6): 847-849.
Barthel-Rosa, L. P. et al. (1999). "Chemistry in Fluorous Media: A User's Guide to Practical Considerations in the Application of Fluorous Catalyst and Reagents," *Coordination Chemistry Review* 190-192:587-605.
Berendsen, G. E. et al. (1980). "(Hepatadecafluorodecyl) Dimethylsilyl Bonded Phase For Reversed-Phase Liquid Chromatography." *Anal. Chem.* 52:1990-1993.
Bergbreiter, D. E. et al. (1991). "Catalytic Cyclopropanation with Transition Metal Salts of Soluble Polyethylene carboxylates," *Tetrahedron Letters* 32(24):2731-2734.
Bergbreiter, D. E. et al. (2000). "Fluoroacrylate-Bound Fluorous-Phase Soluble Hydrogenation Catalysts." *Organic Letters* 2(3): 393-395.
Bertrand, J. A. et al. (1966). "A Study of Bis(Hexafluoroacetylacetona) To Copper(II)," *Inorg. Chem.*5(3): 489-491.
Bertucco, A. (1999). "Precipitation and Crystallization Techniques" Chapter 2.3 *In Chemical Synthesis using Supercritical Fluids*, Jessop and Leitner, Eds, Wiley-VCH, pp. 108-126 (Includes Table of Contents).
Betzemeier, B. et al. (1998). "Wacker Oxidation Of Alkenes Using A Fluorous Biphasic System. A Mild Preparation Of Polyfunctional Ketones." *Tetrahedron Letters* 39(37): 6667-6670.
Betzemeier, B. et al. (2000). "Copper-Catalyzed Aerobic Oxidation Of Alcohols Under Fluorous Biphasic Conditions." *Tetrahedron Letters* 41(22): 4343-4346.
Bhattacharyya, P. et al. (2000). "Phosphorus (III) Ligands In Fluorous Biphase Catalysis," *Journal of Fluorine Chemistry* 101(2): 247-255.
Billiet, H. A. H. et al. (1981). "Retention And Selectivity Characteristics Of A Non-Polar Perfluorinated Stationary Phase For Liquid Chromatography." *J. Chromatogr.* 218:443-454.
Brown, R. A. et al., (2001)."Asymmetric Hydrogenation and Catalyst Recycling Using Ionic Liquid and Supercritical Carbon Dioxide," *J. Am. Chem.* 123:1254-1255.
Cavazzini, M. et al. (1999). "Perfluorocarbon-Soluble Catalyst and Reagents and the Application of FBS (Fluorous Biphase System) to Organic Synthesis," *Journal of Fluorine Chemistry* 94:183-193.
Chen, W. P. et al. (2000). "Fluorous Soluble Polymer Catalysts For The Fluorous Biphase Hydroformylation Of Olefins." *Chemical Communications* (10): 839-840.

(Continued)

*Primary Examiner*—Edward M Johnson
(74) *Attorney, Agent, or Firm*—Morrison & Foerster LLP

(57) ABSTRACT

Methods of enhancing the solubility of a fluorinated compound in an organic solvent are provided. In one embodiment, carbon dioxide gas pressure is applied to the solvent at a pressure effective to enhance the solubility of the fluorinated compound. The method may further include recrystallizing the fluorinated compound by reducing the pressure of the carbon dioxide gas. Also provided are methods of conducting a reaction using a fluorinated compound in an organic solvent. In one embodiment, the method comprises applying carbon dioxide pressure to an organic solvent comprising at least one substrate and a fluorinated catalyst, in an effective amount to solubilize the catalyst; and permitting the fluorinated catalyst to catalyze the reaction of the substrate to form a product. The catalyst is optionally separated from the reaction product and solvent after the reaction by the release of the pressure.

45 Claims, 4 Drawing Sheets

OTHER PUBLICATIONS

Consani, K. A. et al. (1990). "Observations on the Solubility of Surfactants and Related Molecules in Carbon Dioxide at 50 Degrees Celsius," *The Journal of Supercritical Fluids* 3:51-65.

Crich, D. et al. (1999). "Design Synthesis, Application And Recovery Of A Minimally Fluorous Diaryl Diselenide For The Catalysis Of Stannane-Mediated Radical Chain Reactions," *Tetrahedron* 55(50): 14261-14268.

Curran, D. et al. (Feb. 2001). "Fluorous Techniques for the Synthesis and Separation of Organic Molecules," *Green Chemistry* G3-G7.

De Wolf, E. et al. (1999). "Fluorous Phase Separation Techniques in Catalysis," *Chem, Soc. Rev.* 28(1): 37-41.

Dimagno, S. G. et al. (1996). "Fluorous Biphasic Singlet Oxygenation With A Perfluoroalkylated Photosensitizer." *Journal of the American Chemical Society* 118(22):5312-5313.

Dinh, L. V. et al. (1999). "Transition Metal Catalysis In Fluorous Media: Extension Of A New Immobilization Principle To Biphasic And Monophasic Rhodium-Catalyzed Hydrosilylations Of Ketones And Enones." *Tetrahedron Letters* 40(51): 8995-8998.

Endres, A. et al. (1999). "A Fluorous Phase Approach To Rhodium-Catalyzed Carbenoid Reactions With Diazoacetates." *Tetrahedron Letters* 40(35): 6365-6368.

Fawcett, J., E. et al. (1997). "Fluorous-Phase Soluble Rhodium Complexes: X-Ray Structure Of [Rhcl(CO)(P(C2H4C6F13)(3)(2)]." *Chemical Communications* (12): 1127-1128.

Field, C. N. et al. (2000). "Precipitation of Solvent-Free C60(CO2)0.95 from Conventional Solvents: A New Antisolvent Approach to Controlled Crystal Growth Using Supercritical Carbon Dioxide," *J. Am Chem. Soc.* 122:2480-2488.

Fish, R. H. (1999). "Fluorous Biphasic Catalysis: A New Paradigm for the Separation of Homogeneous Catalysts from Their Reaction Substrates and Products," *Chem. Eur. J.* 5(6):1677-1680.

Freund, H. et al. (1996). "Crystallization under Gas Pressure" In High Pressure Chemical Engineering Process Technology Proceedings, 12 van Rohr and Trepp, Eds., Elsevier Science B.V. pp. 211-216. (Includes Table of Contents).

Guillevic, M. A. et al. (1997). "Synthesis, Structure, And Oxidative Additions Of A Fluorous Analogue Of Vaska's Complex, Trans-[Ircl(CO){P[CH$_2$CH$_2$(CF$_2$)(5)CF$_3$](3)}(2)]-Altered Reactivity In Fluorocarbons And Implications For Catalysis." *Angewandte Chemie-International Edition in English* 36(15): 1612-1615.

Guillevic, M. A. et al. (1998). "Organometallic Reactivity Patterns In Fluorocarbons And Implications For Catalysis: Synthesis, Structure, Solubility, And Oxidative Additions Of A Fluorous Analogue Of Vaska's Complex, Trans Ir(CO)(CI)[P(CH2CH2(CF2)(5)CF3)(3)](2)." *Organometallics* 17(4): 707-717.

Haddleton, D. M. et al. (2000). "Copper(I)-Mediated Living Radical Polymerization Under Fluorous Biphasic Conditions." *Journal of the American Chemical Society* 122(7):1542-1543.

Herrera, V. et al. (1998). "Tuning The Fluorous Partition Coefficients Of Organometallic Complexes, The Synthesis And Characterization Of [Eta$^5$-C$_5$H$_4$CH$_2$CH$_2$(CF$_2$)$_9$CF$_3$]Rh(CO)L (L=CO Or P[CH2CH2(CF$_2$)$_5$CF$_3$]$_3$) And C12Ni{P[CH$_2$CH$_2$(CF$_2$)$_5$CF$_3$]$_3$}$_2$." *Inorganic Chemistry Communications* 1(6): 197-199.

Hope, E. G. et al. (1999). "Fluorous Biphase Catalysis," *J. Fluorine Chem.* 100: 75-83.

Hope, E. G., R. D. W. Kemmitt, et al. (1999). "The Rhodium Catalysed Hydrogenation Of Styrene In The Fluorous Biphase." *Journal of Fluorine Chemistry* 99(2): 197-200.

Horvath, I. T. et al. (1994). "Facile Catalyst Separation Without Water—Fluorous Biphase Hydroformylation Of Olefins." *Science* 266(5182): 72-75.

Horvath, I. T. et al. (1998). "Molecular Engineering In Homogeneous Catalysis: One-Phase Catalysis Coupled With Biphase Catalyst Separation. The Fluorous-Soluble HRh(CO){P[CH$_2$CH$_2$(CF$_2$)$_5$CF$_3$]$_3$}$_3$ Hydroformylation System." *Journal of the American Chemical Society* 120(13): 3133-3143.

Jessop, P. G. et al., (2001). "Catalysis Using Supercritical or Subcritical Inert Gases Under Split-Phase Conditions," Chapter 8 *In Clean Solvents Alternative Media for Chemical Reactions and Processing,* Abraham, M. A. et al. (eds.), American Chemical Society, Washington, D.C., ACS Symposium Series 819, pp. 97-112.

Juliette, J. J. J. et al. (1999). "Transition Metal Catalysis In Fluorous Media: Practical Ampplication Of A New Immobilization Principle To Rhodium-Catalyzed Hydroborations Of Alkenes And Alkynes." *Journal of the American Chemical Society* 121(12): 2696-2704.

Jerrrick, J. et al. (1997). "Transition Metal Catalysis In Fluorous Media: Practical Application Of A New Immobilization Principle To Rhodium-Catalyzed Hydroboration." *Angewandte Chemie-International Edition in English* 36(15): 1610-1612.

Kalman, D. et al. (1980). "On-Column Cryogenic Trapping of Sorbed Organics for Determination by Capillary Gas Chromatography," *Anal. Chem.* 52:1993-1994.

Kane, M. A et al. (2000). "Effects of Added $CO_2$ on the Conformation of Pyrene End-Labeled Poly(dimethylsiloxane) Dissolved in Liquid Toluene," *J. Phys. Chem.* 104:8585-8591.

Kleijn, H. et al. (1999). "Synthesis Of Arylzinc Thiolates Containing Perfluoroalkyl Chains. Model Catalyst Precursors For The Enantioselective Zinc-Mediated 1,2-Addition Of Dialkylzincs To Aldehydes In Fluorous Biphase Systems." *Organic Letters* 1(6): 853-855.

Kleijn, H. et al. (1998). "Ortho-Bis(Animo)Arylnickel(II) Halide Complexes Containing Perfluoroalkyl Chains As Model Catalyst Precursors For Use In Fluorous Biphase Systems." *Tetrahedron* 54(7): 1145-1152.

Laintz, E. E. et al. (1991). "Solubility of Fluorinated Metal Diethyldithiocarbamates in Supercritical Carbon Dioxide," *The Journal of Supercritical Fluids* 4:194-198.

Li, C. B. et al. (1998). "Solution Thermochemical Study Of A Fluorous Tertiary Phosphine Ligand In Rhodium And Ruthernium Systems," *Organometallics* 17(3): 452-456.

Liu, J. et al. (2001). "Polymerization of Styrene in Solutions with Compressed Carbon Dioxide as Antisolvent," *J. Supercritical Fluids* 20: 171-176.

Luo, Z. et al., (2001). "Fluorous Mixture Synthesis: A Fluorous-Tagging Strategy for the Synthesis and Separation of Mixtures of Organic Compounds," *Science* 251(5509)1766-1769.

Nakamura, Y. et al. (2000). "Asymmetric Alkylation Of Aromatic Aldehydes With Diethylzinc Catalyzed By A Fluorous BINOL-Ti Complex In An Organic And Fluorous Biphase System." *Tetrahedron Letters* 41(1): 57-60.

Pozzi, G. et al. (1997). "Cobalt Tetraarylporphyrin-Catalysed Epoxidation Of Alkenes By Dioxygen And 2-Methylpropanal Under Fluorous Biphasic Conditions," *Chemical Communications* (1): 69-70.

Pozzi, G. et al. (1997). "Metal Complexes Of A Tetraazacyclotetradecane Bearing Highly Fluorinated Tails: New Catalysts For The Oxidation Of Hydrocarbons Under Fluorous Biphasic Conditions," *Tetrahedron Letters* 38(43): 7605-7608.

Quici, S. et al. (1999). "Synthesis Of Perfluoroalkylated Bipyridines—New Ligands For Oxidation Reactions Under Fluorous Triphasic Conditions." *Tetrahedron Letters* 40(18): 3647-3650.

Reverchon, E. (1999). "Supercritical Antisolvent Precipitation of Micro- and Nano-particles," *Journal of Supercritical Fluids* 15:1-21.

Richter, B. et al. (1999). "Fluorous Biphasic Hydrogenation Of 1-Alkenes Using Novel Fluorous Derivatives Of Wilkinson's Catalyst." *Journal of Molecular Catalysis a Chemical* 145(1-2): 317-321.

Richter, B. et al. (2000). "Fluorous Versions Of Wilkinson's Catalyst. Activity In Fluorous Hydrogenation Of L-Alkenes And Recycling By Fluorous Biphasic Separation." *Journal Of The American Chemical Society* 122(16): 3945-3951.

Rutherford, D. et al. (1998). "Transition Metal Catalysis In Fluorous Media: Application Of A New Immobilization Principle To Rhodium-Catalyzed Hydrogenation Of Alkenes." *Catalysis Today* 42(4): 381-388.

Ryu, I. et al. (1997). "Hydroxymethylation Of Organic Halides. Evaluation Of A Catalytic System Involving A Fluorous Tin Hydride Reagent For Radical Carbonylation." *Tetrahedron Letters* 38(45): 7883-7886.

Schurig, V. (1986). "Relative Stability Constants of *Olefin-Rhodium (II)* vs. *Olefin-Rhodium (I)* Coordination As Determined by Complexation Gas Chromatography," *Inorg. Chem.* 25:945-949.

Scott, R. L. (1948). "The Solubility of Fluorocarbons," *J. Am. Chem. Soc.* 70:4090-4093.

Sellin, M. F et al. (2000). "Hydroformylation Reactions in Supercritical Carbon Dioxide Using Insoluble Metal Complexes," *J. Chem Soc. Dalton Trans* pp. 1681-1683.

Spetseris, N. et al. (1998). "Organic/Fluorous Phase Extraction: A New Tool For The Isolation Of Organometallic Complexes." *Organometallics* 17(8): 1458-1459.

Tai, C. Y et al. (1995). "Growth of Naphthalene Crystals from Supercritical $CO_2$ Solution," *AIChE Journal* 41(10):2227-2236.

Tai, C. Y. et al., (1997). "Crystal Morphology and Growth Rate of Naphthalene in Various Processes Involving Supercritical Carbon Dioxide," *Trans IChemE* 75:228.232.

Takeuchi, S. et al. (1998). "Catalytic Enantioselective Protonation Of A Samarium Enolate With Fluorous Chiral And Achiral Proton Sources In Fluorous Biphasic Systems." *Tetrahedron Letters* 39(47): 8691-8694.

Thomas, C. A. et al., (2001). "Hydrogenation of Carbon Dioxide Catalysed by Ruthenium Trimethylphosphine Complexes: Effect of Gas Pressure And Additives on Rate in the Liquid Phase," *Can. J. Chem. IN PRESS* 79:719-724.

Vincent, J. M et al. (1997). "Fluorous Biphasic Catalysis: Complexation Of 1,4,7-[C8F17($CH_2$)(3)](3)-1,4,7-Triazacyclononane With [M($C_8F_{17}$($CH_2$)$_2$$CO_2$)$_2$] (M=Mn, Co) To Provide Perfluoroheptane-Soluble Catalysts For Alkane And Alkene Functionalization In The Presence Of T-BuOOH and $O_2$," *Angewandte Chemie-International Edition in English* 36(21): 2346-2349.

Wende, M. et al., (2001). "Fluorous Catalysis Without Fluorous Solvents: A Friendlier Catalyst Recovery/Recycling Protocol Based Upon Thermomorphic Properties and Liquid/Solid Phase Separation," *J. Am. Chem. Soc.* 123:11490-11491.

METHODS FOR SOLUBILIZING AND RECOVERING FLUORINATED COMPOUNDS

CROSS REFERENCE TO RELATED APPLICATIONS

This application is the U.S. National Phase of PCT International Application No. PCT/US02/17110, filed May 30, 2002, which claims priority to U.S. Provisional Application No. 60/294,909, filed May 30, 2001, the disclosure of each of which are incorporated herein by reference in their entirety.

STATEMENT OF RIGHTS TO INVENTIONS MADE UNDER FEDERALLY SPONSORED RESEARCH

This invention was made with Government support under Grant No. CHE-9815320, awarded by the National Science Foundation. The government has certain rights in this invention.

TECHNICAL FIELD

This invention relates to solvent systems for highly fluorinated compounds which can be used in a variety of applications, such as recrystallization and catalysis.

BACKGROUND ART

Fluorous biphasic catalysis methods have been described in the art. A review of fluorous phase separation techniques in catalysis is described in de Wolf et al., *Chem. Soc. Rev.* 28(1): 37-41(1999); Hope and Stuart, *J. Fluorine Chem.*, 100(1-2): 75-83 (1999); Fish, R. H., *Chem. Eur. J*, 5:1677-1680 (1999); and Barthel-Rosa and Gladysz, *Coord. Chem. Rev.*, 192: 587-605 (1999). Fluorous biphasic catalysis is a method of homogeneous catalysis that allows the catalyst and the products to be separated after the reaction. In this scheme, shown in FIG. 1, a highly fluorinated catalyst is dissolved in a highly fluorinated solvent (the fluorous solvent) and organic reagents are dissolved in a traditional organic liquid. The two liquid solutions are placed together, and the reaction takes place, often requiring heating and stirring. After the reaction, the organic products are removed by pipetting off the organic liquid solution. The catalyst remains in the fluorous liquid. Unfortunately, the fluorous solvents used as the lower liquid phase are usually volatile, environmentally damaging and expensive to replace. An example of fluorous biphasic catalysis is the fluorous biphase hydroformylation of olefins as described in Horváth and Rabai (1994), *Science* 266(5182): 72-75.

Supercritical antisolvent precipitation, in which a solid compound is dissolved in an organic solvent and then made to precipitate as a fine powder by the rapid addition of carbon dioxide gas, has been described in Reverchon, E., *J. Supercrit. Fluids*, 15: 1-21 (1999); Bertucco, A., "Precipitation and crystallization techniques" in *Chemical Synthesis using Supercritical Fluids*; Jessop and Leitner, Eds.; Wiley-VCH: Weinheim, 1999, pp 108-126; and Field et al. *J. Am. Chem. Soc.,* 122, 2480-2488 (2000). The article by Field also described a somewhat slower addition of carbon dioxide gas in order to obtain very small crystals of the solid compound.

Methods of synthesis and separation in which organic/fluorous phase separation techniques are used to effect separations, and compositions of matter comprising fluorous Si, Sn and Ge compounds are described in U.S. Pat. Nos. 6,156,896; 6,376,676; 6,372,906; 5,777,121; and 5,859,247.

Crystallizing under gas pressure, in which an organic compound is made to melt by the addition of carbon dioxide pressure and then is made to crystallize by the slow release of the carbon dioxide, is described in Freund and Steiner, Crystallization under Gas Pressure" in *High Pressure Engineering*, von Rohr and Trepp, Eds., Elsevier Science B. V. (1996). This technique is limited to those few compounds which can be made to melt by carbon dioxide pressure at moderate temperatures. The growth of crystals from supercritical carbon dioxide or related fluids is described in U.S. Pat. No. 4,512,846; Tai and Cheng, *AIChE Journal,* 41:2227-2236 (1995). In this technique, an organic compound such as naphthalene is dissolved in supercritical carbon dioxide and then made to crystallize by slow release of the carbon dioxide pressure. The observation that highly fluorinated metal complexes have good solubility in supercritical carbon dioxide was described in Laintz et al., *J. Supercritical Fluids,* 4:194-198 (1991). The observation that highly fluorinated surfactants have good solubility in carbon dioxide is described in Consani, K. A. and Smith, R. D., *J. Supercrit. Fluids,* 1990, 3: 51-65 (1990). Polymerization of styrene in solutions with compressed carbon dioxide as antisolvent is described in Liu et al., *J. Supercritical Fluids,* 20:171-176 (2001).

Fluorous solvents are disadvantageous because of their long lifetime in the environment, high cost, and contribution to the greenhouse effect. It would be advantageous if the use of fluorous solvents could be avoided in solvation, recrystallization and catalytic reaction techniques using fluorinated compounds.

SUMMARY OF THE INVENTION

Methods of enhancing the solubility of a fluorinated compound in an organic solvent are provided. In one embodiment, the solvent is non-halogenated. In one embodiment, the method comprises applying carbon dioxide gas to the solvent at a pressure effective to enhance the solubility of the fluorinated compound. The pressure of the carbon dioxide gas is, for example, in the range of 30-300 bar, or in the range of 40-90 bar. The organic solvent is or comprises, for example, pentane, hexane, heptane, octane, nonane, decane, cyclopentane, cyclohexane, dioxane, benzene, toluene, xylene, ether, diisopropylether, ethyl acetate, tetrahydrofuran, triethylamine, tripropylamine, N,N,N',N'-tetramethylethylenediamine, methylene chloride, chloroform, chlorobenzene, acetone, nitrobenzene, acetonitrile, formamide, acetamide, dimethylformamide, dimethylacetamide, nitromethane, methanol, ethanol, propanol, butanol, isopropanol, sec-butanol, tert-butanol, ethylene carbonate, propylene carbonate, glyme, diglyme, dimethylsulfone, or dimethylsulfoxide, or mixtures thereof The method may further include recrystallizing the fluorinated compound by reducing the pressure of the carbon dioxide gas, for example over 24 hours or less, or over 4 hours or less. The fluorinated compound is for example a catalyst, such as an organic compound or an organometallic complex of a main group metal, main group semimetal, transition metal, actinide or lanthanide. The catalyst can include one or more highly fluorinated ligands or groups.

Also provided are methods of recrystallizing a fluorinated compound in an organic solvent, such as a non-halogenated organic solvent, comprising: applying carbon dioxide gas to the solvent at a pressure effective to enhance the solubility of the fluorinated compound; and recrystallizing the fluorinated compound by reducing the pressure of the carbon dioxide gas, wherein the method further comprises providing a plurality of individual sample containers, each container comprising a fluorinated compound in the solvent, wherein carbon dioxide gas is applied to the solvent in the individual sample containers at a pressure effective to enhance the solubility of the fluorinated compound; and wherein the fluorinated compounds are crystallized in the individual sample containers by reducing the pressure of the carbon dioxide gas. The components of the individual samples can be varied. For example, the concentration or compound(s) or solvent(s) can be varied. The method may further include screening the recrystallized fluorinated compounds for crystallinity or purity.

In another embodiment, there is provided a method of conducting a reaction using a fluorinated compound in an organic solvent, the method comprising applying carbon dioxide gas to the organic solvent at a pressure effective to solubilize the fluorinated compound during the reaction. In one embodiment, the solvent is non-halogenated. The pressure of the carbon dioxide gas is for example in the range of 40 to 90 bar. The fluorinated compound is for example a catalyst. Optionally, a plurality of reactions are conducted, wherein, for example, different reaction conditions, such as reagents, concentration, solvent, or pressure are varied.

Methods of conducting a reaction in one embodiment comprise applying carbon dioxide pressure to an organic solvent comprising at least one substrate and a fluorinated catalyst, in an effective amount to solubilize the catalyst; and permitting the fluorinated catalyst to catalyze the reaction of the substrate to form a product. The carbon dioxide can be applied to the solvent at a pressure for example in the range of 40 to 90 bar. The method may include reducing the carbon dioxide gaseous pressure, thereby to cause precipitation of the catalyst, and optionally recovering the catalyst from the reaction product mixture. Examples of reactions include hydrogenation, hydroboration, hydroformylation, cyclopropanation, C—H insertion reactions, oxidation, hydroxylation, isomerization, coupling reactions, olefin metathesis, polymerization, hydrosilylation, hydrocyanation, epoxidation, and Diels-Alder reactions. The catalyst is, for example, an organic compound or an organometallic complex of a main group metal, main group semimetal, transition metal, actinide or lanthanide. In one embodiment, the solvent is non-halogenated. In one embodiment, a fluorous support or polymer is present in order to help trap the catalyst upon release of the $CO_2$ pressure.

In one embodiment a method of conducting a reaction using a fluorinated compound in an organic solvent is provided, comprising applying carbon dioxide gas to an organic solvent, such as a non-halogenated organic solvent, comprising a fluorinated compound, at a pressure effective to solubilize the fluorinated compound during the reaction; permitting the catalyst to catalyze the reaction of the substrate to form a product; and reducing the carbon dioxide gaseous pressure, thereby to cause precipitation of the catalyst; wherein the method further comprises including a fluorinated support material in the organic solvent, wherein the fluorinated support material is capable of adsorbing the catalyst when the carbon dioxide pressure is reduced.

The fluorinated support material is for example a fluorinated polymer, or an inorganic or organic support material comprising fluorinated organic groups that may be attached to the inorganic or organic support material.

The method may comprise, for example, applying carbon dioxide pressure to a non-halogenated organic solvent comprising at least one substrate and a fluorinated organometallic catalyst, in an effective amount to solubilize the catalyst; providing a fluorinated support material in the solvent; permitting the catalyst to catalyze the reaction of the substrate to form a product; and reducing the carbon dioxide gaseous pressure, thereby to permit precipitation of the catalyst and adsorption of the fluorinated catalyst on the support material. The support material having the fluorinated catalyst thereon optionally may be separated from the solvent, and optionally reused to catalyze one or more additional reactions, thus enabling efficient recovery and recycling of the catalyst.

The fluorinated catalyst may be adsorbed onto the support material prior to application of the carbon dioxide pressure, and released from the support material after application of the carbon dioxide pressure.

The method may include comprises conducting a plurality of the reactions, wherein individual reactions vary in reaction conditions. The plurality of reactions may be done in plural different reaction containers, wherein individual reaction containers comprise an organic solvent, at least one reaction substrate, and a fluorinated organometallic catalyst, and wherein the method comprises: applying carbon dioxide pressure to the reaction containers in an effective amount to solubilize the catalyst; permitting the catalyst to catalyze the reaction of the substrate to form a product in the reaction containers; and reducing the carbon dioxide gaseous pressure, thereby to cause precipitation of the catalyst, and wherein optionally a fluorinated support material is provided in the solvent.

The reaction containers may be provided within one or more sealable reaction vessels. The amount or identity of at least one of the organic solvent, the reaction substrate, or the catalyst may vary in the different reaction containers. The method may further include screening the reaction for a reaction product in the individual containers.

DETAILED DESCRIPTION

Figure 1:
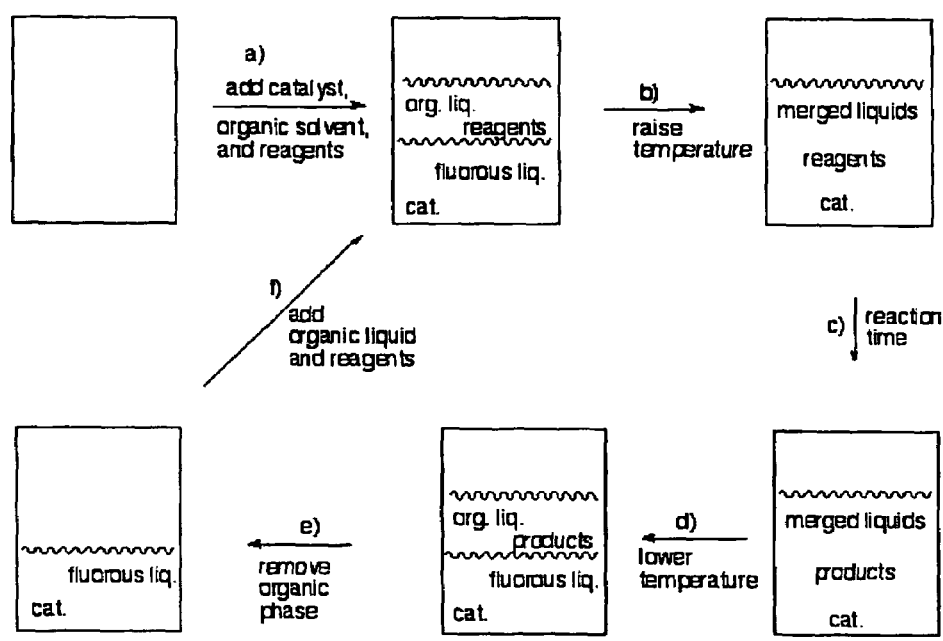
FIG. 1 is a scheme illustrating fluorous biphasic catalysis.

Provided are methods to enhance the solubility of a fluorinated compound in an organic solvent. In one embodiment, the fluorinated compound is fully or partially insoluble in an organic solvent, and application of carbon dioxide gas pressure to the solvent, to form a $CO_2$-expanded solvent, results in enhanced solubility of the fluorinated compound in the solvent. Thus, methods are provided for solubilizing a fluorinated compound in an organic solvent by applying carbon dioxide gas to the solvent at a pressure effective to solubilize the fluorinated compound. Preferably, the fluorinated compound is completely solubilized in the solvent. In one application, after application of the gaseous carbon dioxide pressure, the fluorinated compound can be recrystallized by reducing the pressure of the carbon dioxide gas. Optionally, the solubility of a reactant, product or catalyst in a solvent during a reaction can be enhanced.

Also provided are methods of conducting a reaction using a fluorinated compound in an organic solvent. In one embodiment, the method comprising applying carbon dioxide gas to the organic solvent at a pressure effective to enhance the solubility of the fluorinated compound, and preferably completely solubilize the fluorinated compound.

As used herein "fluorinated compound" refers to a compound containing one or more fluorine atoms, for example comprising carbon fluorine bonds. The fluorine atoms may be present or introduced to the compound by any of a variety of methods known in the art. Fluorinated compounds include organic and inorganic compounds, including coordination or organometallic complexes. In one embodiment the fluorinated compound may be a catalyst, such as an inorganic, organic or organometallic catalyst.

Fluorinated catalysts include complexes such as $RhCl(P(C_6H_4R_f)_3)_3$, $RhCl(P(CH_2C-H_2R_f)_3)_3$, $RuHCl(P(C_6H_4R_f)_3)_3$, and $RuHCl(P(CH_2CH_2R_f)_3)_4$, which are catalysts for hydrogenation, $RhCl(P(CH_2CH_2R_f)_3)_3$, which is a catalyst for hydroboration, $Rh(H)(CO)(P(CH_2CH_2R_f)_3)_3$, which is a catalyst for hydroformylation, complexes 1 and 2 which are catalysts for cyclopropanation and C—H insertion reactions, and complex 3, which is a catalyst for oxidation reactions. $R_f$ is as defined below.

Examples of fluorinated compounds include:

a) Completely or partially fluorinated alkanes, alkenes, alkynes, diene, enyne, diyne, aromatic, or related compound based upon saturated or unsaturated hydrocarbons but containing attached fluorine atoms or attached $R_f$ groups as defined below, (e.g. perfluorohexane $C_6F_{14}$, perfluoro(methylcyclohexane) $CF_3C_6F_{11}$, poly(tetrafluoroethylene) $(CF_2CF_2)_n$, hexafluorobenzene, perfluorokerosene, and nonafluorobutylbenzene $(F(CF_2)_4C_6H_5)$;

b) Completely or partially fluorinated alcohols $R_fOH$ (such as perfluorodecanol $F(CF_2)_{10}OH$ or 1H,1H,2H,2H-perfluorooctan-1-ol $F(CF_2)_6CH_2CH_2OH$), where $R_f$ is a partially or completely fluorinated chain (alkyl, aryl, ether, ester or the like) such as $(CF_2)_nF$, $CH_2CH_2(CF_2)_nF$, $C_6H_4(CF_2)_nF$, $C_6H_4CH_2CH_2(CF_2)_nF$, $(CF_2CF_2O)_nCF_3$, or $(CF_2CF_2O_2C)_nCF_3$. $R_f$ can be branched or linear. $R_f$ can be saturated or unsaturated. $R_f$ can be nonpolymeric, oligomeric or polymeric, and n is for example an integer from 0 to 100 e.g. from 1 to 16;

c) Completely or partially fluorinated carboxylic acids $R_fCO_2H$, ethers $R_fOR_f'$ or $R_fOR''$, esters $R_fCO_2R_f'$ or $R_fCO_2R''$ or $R''CO_2R_f$, or similarly substituted or partially substituted amines, imines, amides, ketones, diones, phosphines, phosphites, phosphates, phosphine oxides, thiols; sulfides, sulfoxides, sulfones, nitriles, etc. where $R_f$ is as defined above and $R_f'$ is a similar but not necessarily identical group, and R'' is a nonfluorinated group;

d) Completely or partially fluorinated diones, or related compounds based upon diones but containing attached fluorine atoms or attached $R_f$ groups as defined above, such as 5H,5H-perfluorononane-4,6-dione;

e) Completely or partially fluorinated aromatic, cyclopentadiene, olefin, diene, polyene, or other compound based upon unsaturated hydrocarbons but containing attached fluorine atoms or attached $R_f$ groups as defined above;

f) Completely or partially fluorinated analogs of other classes of ligands or reagents commonly used in homogeneous catalysis, metal extraction, combinatorial chemistry, organic synthesis, and organometallic chemistry; and g) Coordination complexes or organometallic complexes of main group metals or semimetals, transition metals, actinides or lanthanides bearing one or more fluorinated ligands. The fluorinated ligands may be fluorinated compounds such as listed above or anions formed therefrom. The complexes may also bear one or more nonfluorinated ligands or ligands of low fluorine content. Specific examples of complexes include complexes 1-4, $RhCl(P(C_6H_4R_f)_3)_3$, $RuHCl(P(CH_2CH_2R_f)_3)_4$, and $Rh(H)(CO)(P(CH_2C-H_2R_f)_3)_3$. Specific examples of metals include Ti, Zr, V, Cr, Mo, W, Mn, Re, Re, Ru, Os, Co, Rh, Ir, Ni, Pd, Pt, Au, Sm, and Eu. Specific examples of nonfluorinated ligands are H, Cl, Br, CO, $P(CH_3)_3$, $P(C_6H_5)_3$, $C_2H_4$, and $CH_3S(O)CH_3$.

Highly fluorinated compounds such as catalysts can be recrystallized in $CO_2$-expanded organic solvents and used in catalytic reactions. As used herein "highly fluorinated compound" refers to a compound that contains sufficient fluorine atoms in the molecule to make the compound have appreciable solubility in fluorous liquids. The percent fluorine by mass is, for example, about 20% to 100%, e.g., about 30% to 80%. The percent fluorine would depend on the structure of the compound. A fluorous liquid is a liquid compound containing a large proportion of fluorine atoms, or a liquid mixture of such compounds. Fluorous liquids are typically but not always analogs of traditional organic solvents with some or all of the hydrogen atoms replaced by fluorine atoms.

Organic solvents include alkanes, aromatic compounds, alcohols, ethers, ketones, nitroalkanes, nitroaromatics, sulfoxides, carbonates, amides, amines, nitriles, esters, chlorocarbons, chlorohydrocarbons, other halogenated liquids, and ionic liquids. Preferably the organic solvents are non-halogenated. Specific examples of solvents include hexane, cyclohexane, dioxane, carbon tetrachloride, benzene, toluene, ether, chloroform, ethyl acetate, tetrahydrofuran, methylene chloride, acetone, methanol, nitrobenzene, acetonitrile, dimethylformamide, nitromethane, dimethylsulfoxide and N-methyl-N-butylimidazolium hexafluorophosphate, as well as mixtures thereof.

The pressure of the carbon dioxide gas sufficient to enhance the solubility of the fluorinated compound, and preferably sufficient to completely solubilize the fluorinated compound is, for example, about 30 to 300 bar, for example, 40 to 90 bar.

The minimum $CO_2$ pressure that is useful will depend on the choice of fluorinated compound, the amount of fluorinated compound, the choice of solvent, the amount of solvent, and the temperature. Based on the teachings of this disclosure, without undue experimentation, the appropriate conditions could be selected for a particular fluorinated compound.

Expansion of an organic solvent by the application of gaseous (subcritical) $CO_2$ increases the fluorophilicity of the solvent to such an extent that the solvent is able to dissolve highly fluorinated complexes. This method makes it possible to recrystallize such complexes, for example, for the purposes of isolation, purification and X-ray crystallography. It also permits a reaction/separation method similar to fluorous biphasic catalysis but without the need for environmentally damaging fluorous solvents.

An expanded liquid or an expanded solvent is a liquid or solvent in which sufficient gas has dissolved to cause the volume of the liquid phase to expand. The degree of expansion for a typical organic solvent would be from 10% to 3000% or 30 to 3000% by volume, although the degree of expansion of an ionic liquid would be far lower, typically 2% to 50%. The gas could be carbon dioxide, ethane, fluoroform, propene, or any gas having a critical temperature within 100° C. or 100 K of the temperature at which the experiment is to be performed. The enhancement of the fluorophilicity of the liquid is only likely to be observed if the gas is carbon dioxide or a fluorinated gas such as fluoroform ($CHF_3$). Carbon dioxide is preferred.

Recrystallization Methods

The methods of the invention can be used to recrystallize fluorinated compounds, particularly highly fluorinated compounds, such as highly fluorinated catalysts.

In one embodiment, a highly fluorinated complex is placed in a high pressure vessel, along with an amount of organic liquid solvent. The amount of liquid solvent should be so small that the complex is unable to dissolve to a large extent in the liquid solvent. Gaseous $CO_2$ pressure is applied, so that $CO_2$ dissolves in the organic liquid to such an extent that the liquid becomes able to dissolve the complex. It is not necessary, and indeed is not preferred, to raise the pressure so high that a substantial portion of the organic liquid dissolves into the $CO_2$. Stirring may be performed to increase the rate of dissolution of the $CO_2$ into the solvent and the rate of dissolution of the complex into the $CO_2$-expanded liquid solvent. After sufficient time has passed to allow for complete dissolution of the complex, the stirring should cease and the $CO_2$ pressure may be released as slowly and as isothermally as possible, if large crystals are desired. After $CO_2$ pressure release is complete, the vessel is opened up. Particularly large crystals can be obtained by leaving the vessel undisturbed for several hours or days after the pressure release is complete. If a fine powder is desired, then $CO_2$ release could be rapid or the expanded liquid solution could be released from the vessel through an open valve or orifice.

The temperature is, for example, −50° C. to 200° C., e.g., 0° C. to 100° C.

In some instances, it is more advantageous to release the carbon dioxide pressure more quickly, for example, in 4 hours or less, 1 hour or less, or about 1 to 4 hours, if by doing so a supersaturated solution of the fluorous compound in the solvent is thus obtained. Leaving such a solution undisturbed for several days after the $CO_2$ pressure release may result in the formation of crystals.

Rapid Screening of Recrystallization

In another embodiment, a method of screening different recrystallization conditions is provided. In this embodiment, a plurality of samples of a fluorinated compound are recrystallized as disclosed herein in a solvent, such as an organic solvent, such as an organic non-halogenated solvent. The recrystallization conditions are varied in the plural samples, and then the products of the recrystallization are screened for properties, such as crystallinity.

In one embodiment, plural samples are provided that each include a fluorinated compound, such as a fluorinated complex, and a solvent. The plural samples are for example placed in open vials or wells within a pressure vessel or chamber, with or without a stir bar or impeller in each vial or well. Carbon dioxide gas is applied to the samples at a pressure effective to enhance the solubility of the fluorinated compound, and then the pressure of the carbon dioxide gas is reduced to recrystallize the fluorinated compound. Components of the samples, such as the identity or concentration of the compound, or the solvent, are varied in the different samples. The products of the recrystallization method are then screened for a property, such as crystallinity, or purity, such as chemical or optical purity. For example, visual, microscopic, or diffraction measurements may be used to evaluate crystallinity. Spectroscopic or chromatographic methods can be used to evaluate chemical purity or optical purity. In particular, appropriate techniques for determining crystallinity would be visual or microscopic methods, or neutron or X-ray diffraction. In particular, appropriate techniques for determining chemical purity or optical purity would include thin-layer chromatography, column chromatography, liquid chromatography, high pressure liquid chromatography, supercritical fluid chromatography, gas chromatography, gel permeation chromatography, electrophoresis, nuclear magnetic resonance spectroscopy, ultraviolet spectroscopy, visible spectroscopy, infrared spectroscopy, polarimetry, circular dichroism spectroscopy, melting point or boiling point determination, osmometry, or other spectroscopic or chromatographic technique or colligative property measurement. Optical purity can be evaluated, for example, by liquid chromatography including high pressure liquid chromatography, supercritical fluid chromatography, gas chromatography, nuclear magnetic resonance, polarimetry, and circular dichroism spectroscopy.

In the individual samples, recrystallization conditions that can be varied in the different samples include one or more of, concentration or identity of the fluorinated compound, such as a catalyst or the choice or amount of solvent. If more than one such screening experiment is performed, the experiments can differ in terms of the time of application or time taken to release $CO_2$ pressure. A plurality of samples can be screened for recrystallization, for example, 2 or more, 10 or more, 20, or more, 50 or more or 100 or more.

Rapid screening can be conducted to determine optimal conditions for crystallization. For example, crystallization of a fluorinated compound, such as a fluorinated Rhodium complex, can be conducted in an organic solvent or solvent mixture, such as a toluene/DMF mixture, by stirring with a stir bar in a small (eg. 1 dram) vial inside a steel pressure vessel, such as those available commercially (e.g., a 160 mL vessel such as the Model 4772 built by Parr Instrument Company). Additional glass vials are also prepared wherein the components are varied. For example, the solvent or solvent ratios are varied, or the concentration of the fluorinated complex is varied. Different proportions of the organic liquid (such as a heavy alkane, cycloalkane or toluene) and the fluorinated compound may be placed in each vial, along with a micro stir bar.

The vessel is optionally warmed, for example, to 35° C. and $CO_2$ (e.g., 20-80 bar, e.g., 68 bar) is added. The solvent in the vials is optionally stirred magnetically but the stirring is optionally stopped before the $CO_2$ pressure is released. The vent valve to the vessel is opened, for example, slightly so that approximately 1 ml of $CO_2$ gas escapes per minute, for example over one week. The vessel is opened, and then the crystals can be screened and analyzed, for example, crystallographically. Alternatively, and sometimes more effectively, the $CO_2$ pressure is released over 1 to 4 hours, after which the vessel is opened, the vial capped tightly, and the vial left undisturbed for example, for a week. The vials can optionally be placed only one per pressure vessel, and thus pressurized, to avoid cross-contamination if the solvents or fluorinated compounds have significant volatility.

Catalytic Methods

Reactions can be conducted using a fluorinated compound in a solvent, such as an organic solvent, using the methods of the invention. For example, carbon dioxide gas pressure is applied to the organic solvent at a pressure effective to enhance the solubility of the fluorinated compound, and preferably completely solubilize the fluorinated compound during the reaction.

The methods of the present invention have the advantages of fluorous biphasic catalysis without the need for a fluorous liquid solvent. Highly fluorinated homogeneous catalysts are typically insoluble in organic liquids. Application of $CO_2$ pressure is used to render them soluble. Thus catalytic systems are provided which are monophasic (homogeneous) during the catalysis and can be made biphasic (heterogeneous) after the reaction by release of the $CO_2$ pressure. The precipitation of the catalyst thus caused allows facile separation of the catalyst from the products.

In one embodiment, a highly fluorinated catalyst is placed in a high pressure vessel, along with a solution of the organic reagents in an organic liquid solvent. No fluorous solvent is added, or is required, unlike conventional fluorous biphasic catalysis processes. Gaseous $CO_2$ pressure is applied, so that $CO_2$ dissolves in the organic liquid to such an extent that the liquid phase becomes more "fluorophilic" and therefore becomes able to dissolve the highly fluorinated catalyst. The reaction then takes place. Afterwards, the $CO_2$ pressure is released, the organic solvent loses it fluorophilicity, and the catalyst precipitates. The solution is then optionally removed from the vessel through a filter, membrane, filtering material, or powder, which catches the insoluble catalyst but allows the organic solvent and organic products to pass through.

Figure 2:
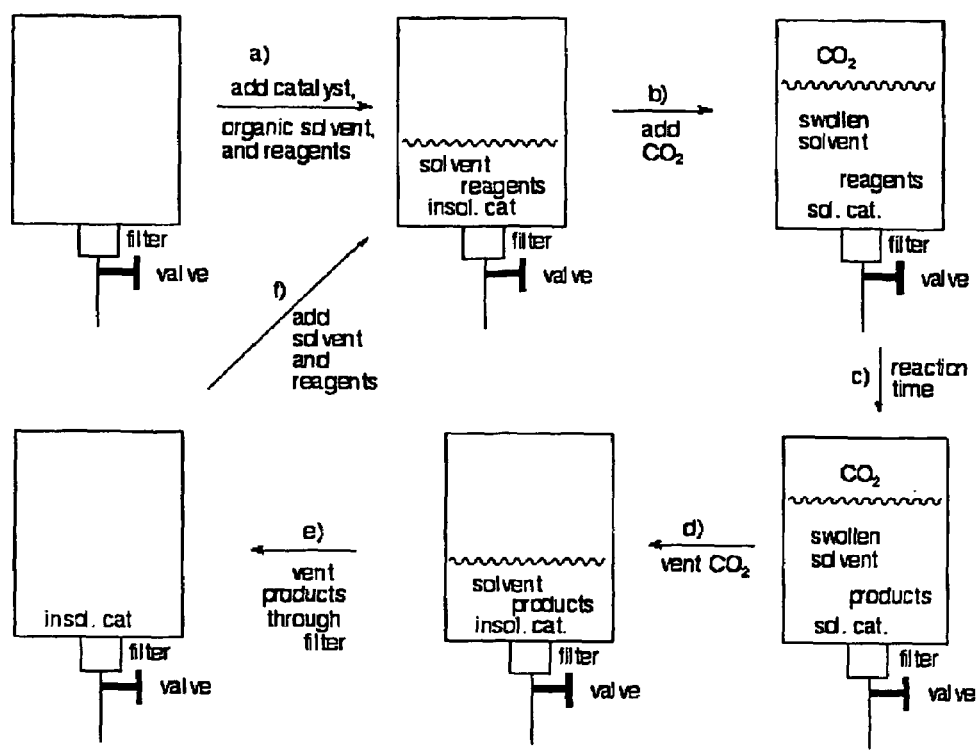
FIG. 2 is a scheme illustrating catalysis methods using expanded solvents.

The process for homogeneous catalysis with catalyst recovery using a fluorinated catalyst but no fluorous solvent is illustrated by way of example in FIG. 2. a) A fluorinated compound, for example, highly fluorinated catalyst, an organic liquid solvent, and other reagents for the reaction are placed in a vessel. At this stage, the catalyst is typically insoluble in the organic solvent. b) $CO_2$ pressure is added, causing the organic liquid to expand in volume and to become more fluorophilic, thereby allowing the fluorinated catalyst to dissolve in the organic phase. c) After enough time has elapsed for the reaction to take place, the solution contains products plus optionally some excess reagent(s). d) The $CO_2$ pressure is vented, so that the solvent returns to approximately its original volume, and the catalyst precipitates. e) The solution is vented from the vessel through a filter. This can be, for example, placed at the bottom of the vessel (as shown) or, for example, could be a filtered line entering the liquid phase from above. The filter catches the insoluble catalyst, while the solution of reaction products passed through the filter. The vessel is therefore empty except for the catalyst and some residual gas. (f) Fresh organic liquid and reagents are added to start the cycle again.

The temperature is, for example, $-50°$ C. to $200°$ C., e.g., $0°$ C. to $100°$ C.

The catalyst can be isolated by other methods. For example, the filter could also be a membrane. For example, a fluorinated group such as a polymer could be complexed to the catalyst to increase precipitation of the catalyst and reduce its solubility in the organic solvent. A material, such as silica gel with fluorinated polymeric groups on it can be used to capture and precipitate the catalyst. The material may be, for example, a polymer or a solid support, beads or powder that could be added to the reaction vessel to help trap the precipitating catalyst. The filtering material could be glass powder, a glass frit, glass wool, fiberglass, sand, diatomaceous earth, silica gel, powdered alumina, powdered polymer, polymer beads, chromatographic packing, or any like material. The filtering material could be unfluorinated, partially fluorinated or completely fluorinated or could be coated in, could incorporate, or could be attached to fluorous or fluorinated material.

Application of subcritical gaseous carbon dioxide to an organic liquid causes the liquid to expand up to several fold, forming an organic/$CO_2$ liquid phase mixture which is referred to as an "expanded" liquid. Advantageously, the present inventors have discovered that the fluorophilicity of organic solvents is greatly increased by the dissolution of carbon dioxide into the liquid.

Catalytic reactions by fluorinated homogeneous catalysts can be conducted in $CO_2$-expanded organic solvents. Recycling of catalyst is possible. Thus, the catalyst can be collected off the filter or filtering material and reused. The advantage of collecting the catalyst include preventing heavy metals in the catalyst from contaminating the product; recovery and reuse of the catalyst; and recovery of the catalyst in order to recycle its metal content.

Catalytic reactions include hydrogenation, hydroboration, hydroformylation, cyclopropanation, C—H insertion reactions, oxidation, hydroxylation, isomerization, coupling reactions, olefin metathesis, polymerization, hydrosilylation, hydrocyanation, epoxidation, and Diels-Alder reactions.

Rapid Screening of Reactions

In another embodiment, the methods disclosed herein can be used in rapid screening or combinatorial applications. In this embodiment, plural reactions are conducted, wherein each reaction involves the use of a fluorinated compound in a solvent, such as an organic solvent, such as a non-halogenated organic solvent. In the individual reactions, carbon dioxide gas is applied to the solvents in each reaction to solubilize the fluorinated compound in the solvent during the reaction. When a plurality of reactions are conducted, the individual reactions can vary in reaction conditions.

The plurality of reactions may be done in plural different reaction containers. For example, the plural reactant/reagent/solvent/catalyst mixtures are placed in open vials or wells within a pressure vessel or chamber, with or without a stir bar or impeller in each vial or well. For example, each reaction can be conducted in a small (e.g., 1 dram) vial inside a steel pressure vessel, such as those available commercially (e.g., a 160 mL vessel such as the Model 4772 built by Parr Instrument Company). One or more such vials may be placed in such a vessel. The different individual reaction containers may include a solvent, such as an organic solvent, such as a non-halogenated organic solvent; at least one reaction substrate; and a fluorinated organometallic catalyst. Carbon dioxide pressure may be applied to the reaction containers in an effective amount to solubilize the catalyst; the catalyst then is permitted to catalyze the reaction of the substrate to form a product in the reaction containers; and then the carbon dioxide gaseous pressure is reduced, to permit precipitation of the catalyst.

The amount or identity of at least one of the organic solvent, the reaction substrate, the catalyst, the reagent(s), or added ligands may vary in the different reaction containers. For example, the concentration of the catalyst or reaction substrate in different reaction containers can be varied. The solvent selected also can be varied. Optionally, ligands which could potentially modify the catalyst could be added and varied. Optionally, the catalyst and/or reaction substrate can vary. The time of application or time taken to release $CO_2$ pressure also can be varied.

The reaction products in the individual reaction containers may be screened for a property, such as an electrical, morphological, optical, magnetic, biological, medicinal, or chemical property. The reaction products in the individual reaction containers may be screened for purity, including chemical or optical purity, yield, or selectivity for a desired product. In particular, appropriate techniques for determining chemical purity, optical purity, yield, or selectivity would include thin-layer chromatography, column chromatography, liquid chromatography, high pressure liquid chromatography, supercritical fluid chromatography, gas chromatography, gel permeation chromatography, electrophoresis, nuclear magnetic resonance spectroscopy, ultraviolet spectroscopy, visible spectroscopy, infrared spectroscopy, polarimetry, circular dichroism spectroscopy, melting point or boiling point determination, osmometry, or other spectroscopic or chromatographic technique or colligative property measurement.

The plural reaction containers can include for example, 2 or more, 10 or more, 20 or more, 50 or more, or 100 or more reaction containers.

Fluorinated Support Materials

In another embodiment, a fluorinated support material is included in the reaction of a fluorinated compound in a solvent, such as an organic solvent, such as a non-halogenated organic solvent. In reactions involving a fluorinated compound, such as a fluorinated organometallic catalyst, a fluorinated support material may be included in the organic solvent, wherein the fluorinated support material is capable of reversibly binding or adsorbing the compound, such as a catalyst. The reaction may include applying carbon dioxide pressure to a mixture comprising a solvent, at least one reaction substrate, a fluorinated support material and a fluorinated organometallic catalyst; the carbon dioxide being in an effective pressure to solubilize the catalyst; permitting the catalyst to catalyze the reaction of the substrate to form a product; and reducing the carbon dioxide gaseous pressure, thereby to cause adsorption or absorption of the catalyst onto or into the fluorinated support material. The fluorinated support material may release the fluorinated compound at high pressure $CO_2$, for example, 10 to 300 bar or more preferably 15 to 140 bar, and bind or adsorb the fluorinated compound when carbon dioxide pressure is reduced. This advantageously enables the fluorinated compound, such as a fluorinated catalyst, to be recovered more efficiently from the liquid phase upon completion of the reaction, which is desirable, for example, when the catalyst is expensive.

The fluorinated support material may be, for example, an inorganic or organic solid or gel with partly or completely fluorinated groups attached. For example, the support material may be a fluorous silica or fluorinated polymer. The material may be, for example, a solid, such as particles, or a gel or a film. For example, the material may be a fluorinated stationary phase as used in chromatography to retain fluorinated compounds, as described in Berendsen, G. E.; Pikaart, K. A.; de Galan, L.; Olieman, C. "(Heptadecafluorodecyl) dimethylsilyl bonded phase for reversed-phase liquid chromatography." *Anal. Chem.* 1980, 52, 1990-1993 and Billiet, H. A. H.; Schoenmakers, P. J.; de Galan, L. "Retention and selectivity characteristics of a non-polar perfluorinated stationary phase for liquid chromatography." *J. Chromatogr.*, 1981, 218, 443-454.

The fluorinated support material may be added to the reaction solvent, for example, in the form of particles or a gel. The fluorinated support material optionally may be immobilized on a surface, such as the surface of a reaction container in which the reaction is conducted.

In one embodiment, the method includes applying carbon dioxide pressure to a non-halogenated organic solvent comprising at least one substrate and a fluorinated organometallic catalyst, in an effective amount to solubilize the catalyst; providing a fluorinated support material in the solvent; permitting the catalyst to. catalyze the reaction of the substrate to form a product; and reducing the carbon dioxide gaseous pressure, thereby to permit precipitation of the catalyst and adsorption of the fluorinated catalyst on the support material. The support material having the fluorinated catalyst thereon can be isolated from the solvent, materials dissolved therein, and any other liquids present, for example by filtration or decantation. Advantageously, the support material having the fluorinated catalyst thereon can be reused for subsequent reactions. The fluorinated catalyst adsorbed onto the support material can be added to the solvent prior to application of the carbon dioxide pressure, and releases from the support material after application of the carbon dioxide pressure.

Optionally, the fluorinated catalyst or catalyst precursor may be loaded into or onto the fluorous support material before the fluorinated catalyst and fluorous support material are used for catalysis. This can be achieved optionally by placing the fluorous support material and the fluorinated catalyst together in a solvent in which the fluorinated catalyst is soluble and the fluorous support material is not; after some time the fluorinated catalyst may partition into the fluorous support material. The solvent is then removed, leaving behind the catalyst-loaded support material. Alternatively, the fluorous support material and the fluorinated catalyst are placed in a solvent in which neither is soluble (for example an alkane or cycloalkane solvent), $CO_2$ pressure is applied to cause the fluorinated catalyst to dissolve in the $CO_2$-expanded solvent, and after some time the $CO_2$ pressure is released. During the application of $CO_2$ pressure or during the release of the $CO_2$ pressure the fluorinated catalyst migrates into the fluorous support material. The solvent is then removed, leaving behind the catalyst-loaded support material.

Extraction of a catalyst is possible from a fluorinated support material, such as fluorous silica into a $CO_2$-expanded liquid, followed by reabsorption of the catalyst back into the support material, such as fluorous silica, upon reduction of the $CO_2$-pressure. In one embodiment, fluorous silica gel is prepared by reacting $R_fCH_2CH_2OH$ ($R_f$=poly(hexafluoropropylene oxide) with $SiCl_4$ (alcohol:$SiCl_4$=2:1) as disclosed herein. The fluorous silica gel is added to a solvent including a fluorinated compound, such as a fluorinated complex, such as $Co(O_2CR_f)_2$ (where $R_f$ is a perfluoropolyether tail), in FC-43 (perfluorotributylamine). Reversible extraction may be performed by placing the catalyst-bearing fluorous silica gel in a pressure vessel along with liquid methanol. Gaseous $CO_2$ is added, and coloration of the organic liquid is observed, particularly at 600-800 psi $CO_2$, indicating that the colored complex is extracted from the fluorous silica by the $CO_2$-expanded methanol. After slow release of the $CO_2$, the complex redeposits on the surface of the fluorous silica, as observed by the migration of the color from the liquid to the solid phase.

For example, homogeneously-catalyzed hydrogenation of styrene may be performed to illustrate the method of catalysis and catalyst recycling using $CO_2$ as a solubility trigger, as disclosed herein using the catalyst precursor [RhCl{P($C_6H_4$-p-$CH_2CH_2(CF_2)_6F)_3$}$_3$] (10 mg), degassed styrene (0.080 mL, 100:1 mole ratio to catalyst), degassed cyclohexane (to bring the total volume to 0.2 mL), and fluorous silica (45 mg). The reaction, such as hydrogenation of styrene to ethylbenzene may be repeated, for example, 2, 3, 4, 5, or more times, using the initial batch of catalyst such as Rh catalyst. Chromatographic analysis can be used to show that the hydrogenation is complete after each cycle, demonstrating that the catalyst deactivation or extraction, if any, is not significant enough to adversely affect the yield even after four cycles.

Applications

The fluorinated compounds, such as highly fluorinated complexes, and methods of the invention, have a variety of applications, for example, in homogenous catalysis, metal extraction (e.g., from contaminated soil), metal purification (e.g., uranium), chemical vapour deposition, combinatorial chemistry, organic synthesis, organometallic chemistry, chemistry in supercritical fluids (SCFs), chemistry in fluorous biphasic systems, chemistry in $CO_2$-expanded liquids and related processes. The compounds and methods disclosed herein have particular use in applications where supercritical or liquid carbon dioxide or a partially or fully fluorinated solvent, or a carbon dioxide expanded solvent is used, or in applications where other halogenated solvents such as chlorinated solvents are used, or in applications where a solvent is not needed, such as chemical vapor deposition.

The disclosures of all patent applications, publications and patents referred to herein are incorporated herein by reference in its entirety. The invention will be further understood by the following non-limiting examples.

EXAMPLES

Example 1

Synthesis of Fluorinated Complexes and Observations of Solubility

A. Synthesis

Figure 3:
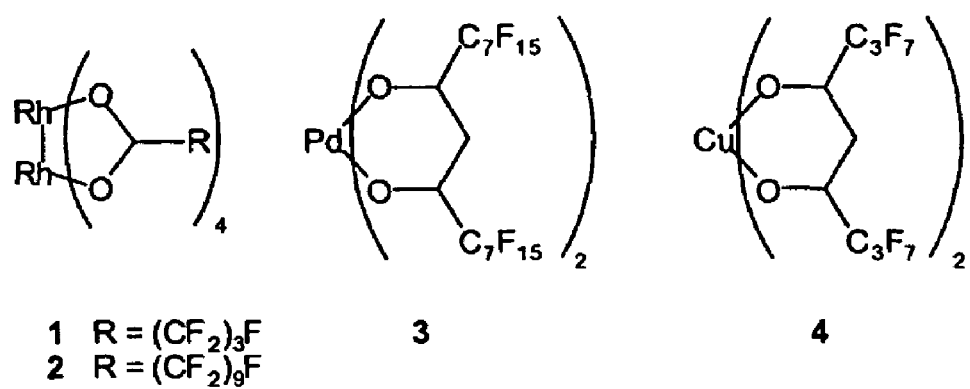
FIG. 3 shows the structure of exemplary fluorinated catalysts.
Figure 4:
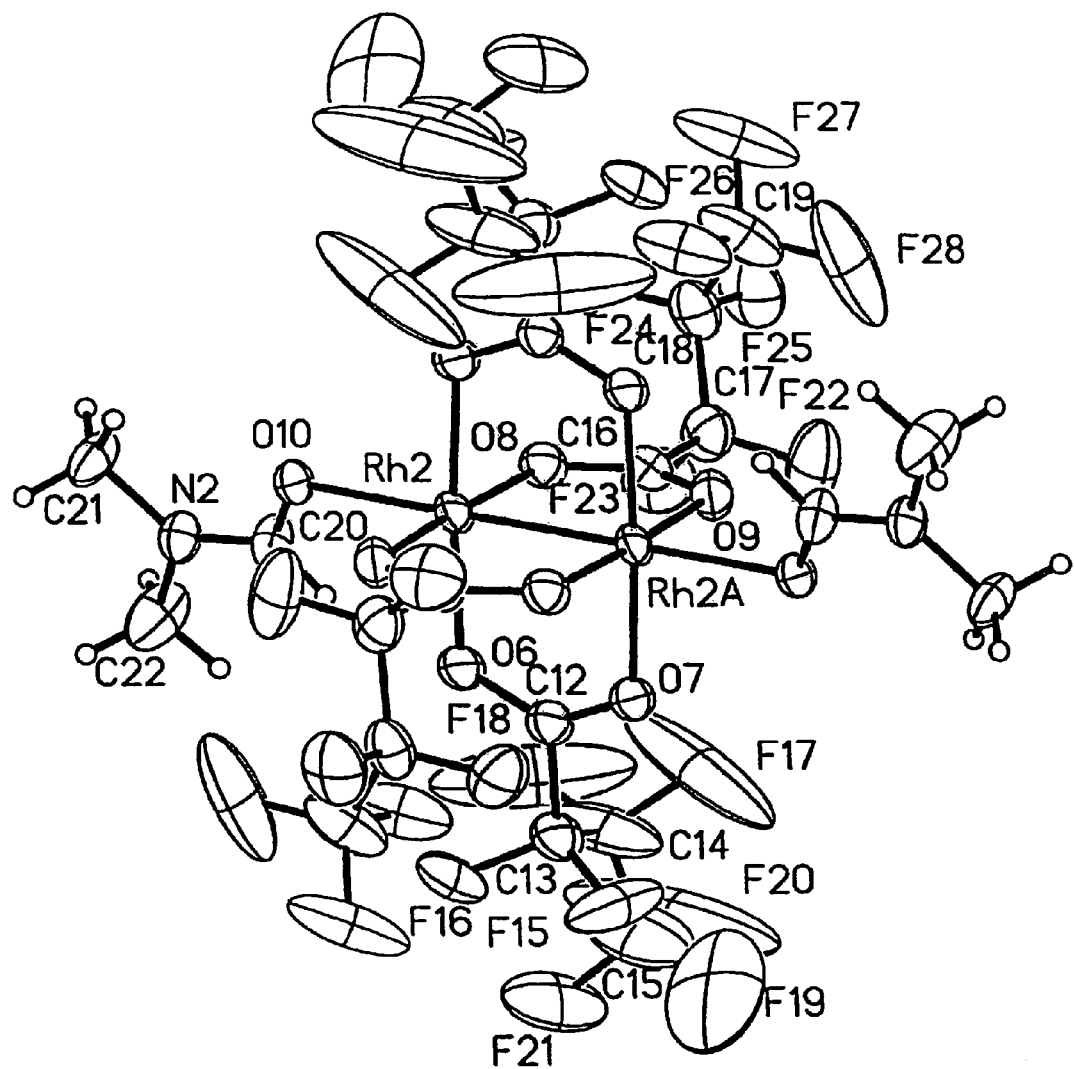
FIG. 4 is an x-ray crystallographic structure of compound 1.

The complex $Rh_2(O_2C(CF_2)_3F)_4$ (complex 1 in FIG. 3) was prepared by the literature method, as described in Schurig, *Inorg. Chem.* (1986), 25, 945.

The bis(methanol) adduct of complex 2 (i.e. $Rh_2(O_2C(CF_2)_9F)_4(MeOH)_2$) was prepared by heating 32 equivalents of $HO_2C(CF_2)_9F$ with 1 equivalent of $Rh_2(OAc)_4$ to 150° C. in a closed vessel without added solvent for 16 h. The green crude product (a mixture of green $Rh_2(O_2C(CF_2)_9F)_4$ and white $HO_2C(CF_2)_9F$) was purified by reprecipitation from methanol, giving blue $Rh_2(O_2C(CF_2)_9F)_4(MeOH)_2$. IR 1650 (s), 1429 (m), 1363 (m), 1214 (s), 1154 (s). Heating the solid blue complex under strong vacuum to 100° C. for one hour gave the green complex $(Rh_2(O_2C(CF_2)_9F)_4$, which regenerates the $Rh_2(O_2C(CF_2)_9F)_4(MeOH)_2$ complex upon contact with methanol.

Complexes 3 and 4 were prepared as described in the literature. Complex 3 was prepared as described in Betzemeier et al., *Tetrahedron Lett.*, 39: 6667-6670 (1998). Complex 4 was prepared as described in Bertrand and Kaplan, *Inorg. Chem.*, 5:489 (1966).

B. Solubility

The bis(methanol) adduct of complex 2 ($Rh_2(O_2C(CF_2)_9F)_4(MeOH)_2$, 64 mg) was placed in a windowed vessel along with a stir bar and 5 mL of cyclohexane, all at 35° C. The solid complex visually appeared to be completely insoluble at 1 atm $CO_2$. $CO_2$ pressure (59 bar) was added, resulting in a marked increase in the volume of the liquid phase and complete dissolution of the coloured complex. The $CO_2$ under these conditions is not supercritical and in the absence of the cyclohexane would not be liquid. The upper phase was gaseous and showed no discoloration, indicating that the complex has no solubility in the gaseous $CO_2$, as expected. When the $CO_2$ pressure was released (slowly, so that the solvent was not lost by entrainment), then the liquid phase returned to its original volume and colour and the complex precipitated. The IR spectrum of the solid was identical to that of the original $Rh_2(O_2C(CF_2)_9F)_4(MeOH)_2$.

Thus, the highly fluorinated complex $Rh_2(O_2C(CF_2)_9F)_4(MeOH)_2$, which is insoluble in cyclohexane, dissolves readily in expanded cyclohexane, and is precipitated again when the $CO_2$ pressure is released. The IR spectrum of the complex after precipitation is identical to that of the starting material. Other complexes were found to exhibit similar behavior, depending on the choice of solvent. For example, complex 3 was insoluble in toluene at 26° C., dissolved in $CO_2$-expanded toluene at 54 bar $CO_2$ and was subsequently precipitated after $CO_2$ release.

Example 2

Catalytic Reactions

Catalytic reactions by fluorinated homogeneous catalysts can be conducted in $CO_2$-expanded organic solvents. The reaction can be compared to the same reaction in the organic solvents under 1 atm of nitrogen. In one embodiment, $CO_2$ can enhance the rate of homogeneously catalysed reactions by merging the phases.

For example, the use of carbon dioxide expanded solvents for cyclopropanation reactions was studied. A preliminary study of fluorous biphasic cyclopropanation was described in Endres, Maas, *Tetrahedron Letters* (1999), 40, 6365.

Cyclohexane is expanded by application of gaseous $CO_2$ pressure to make the cyclohexane a better solvent for dissolving fluorinated catalysts. The application of $CO_2$ pressure is used to accelerate a reaction which is catalyzed by a fluorinated catalyst in a non-fluorous solvent.

The decomposition of ethyl diazoacetate in the presence of styrene shown below was found to be faster in $CO_2$ expanded cyclohexane (25° C., 56 bar $CO_2$, 95% conversion after 40 min) than in normal cyclohexane (25° C., 1 bar $N_2$, 61% conversion).

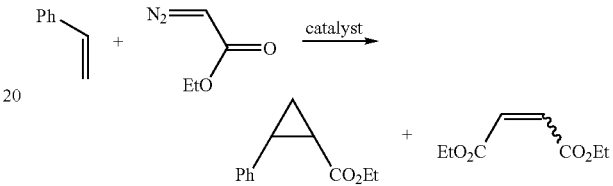

The reaction was performed four times; twice without $CO_2$ and twice with $CO_2$, as shown in Table 1. In each case, $Rh_2(O_2C(CF_2)_9F)_4$ (1.4 µmol), perdeuterated cyclohexane (0.7 or 1.0 mL), styrene (0.56 mmol), ethyl diazoacetate (0.56 mmol), and a microstir bar were placed into a small beaker within a steel pressure vessel. The vessel was warmed to 25° C. and the beaker stirred magnetically. Carbon dioxide pressure was added for two of the runs. After the desired reaction time, the carbon dioxide pressure was released and the reaction mixtures were frozen in liquid nitrogen until such time as they could be analyzed by NMR spectroscopy. The results are summarized in Table 1, where conversion represents the percentage of the ethyl diazoacetate that has been converted into products (primarily dimerization and cyclopropanation products).

TABLE 1

| Run # | Cyclohexane, mL | Stir rate | total time, min | time at 56 bar $CO_2$, min | Conversion, % |
|---|---|---|---|---|---|
| 1 | 0.7 | high | 40 | 23 | 95 |
| 2 | 0.7 | high | 40 | 0 | 61 |
| 3 | 1.0 | low | 30 | 18 | 34 |
| 4 | 1.0 | low | 30 | 0 | 6 |

The results indicate that the $CO_2$ pressure accelerates the reaction.

Example 3

Recrystallization of Fluorinated Compounds

A. Crystallization of a fluorinated complex. Crystals of highly fluorinated complexes were obtained for X-ray crystallography. Structures of such compounds are relatively rare in the literature because the compounds are usually obtained as intractable oils and because of excessive thermal motion or disorder in the fluorinated alkyl chains. Although the latter problem is difficult to avoid, the former problem can be obviated by crystallization of the complexes from $CO_2$-expanded solvents. The bis(N,N-dimethylformamide) adduct of complex 1 was recrystallized from $CO_2$-expanded toluene in the following manner.

Rhodium tetrakis(perfluorobutanoate), $Rh_2(O_2C(CF_2)_3F)_4$, (30 mg, 28 μmol), toluene (0.4 mL), DMF (10 μL), and a small stir bar were placed in a small vial inside a steel pressure vessel. The vessel was warmed to 35° C. and $CO_2$ (68 bar) was added. Pressures as low as 40-50 bar suffice with most compounds, so that the pressure of a $CO_2$ cylinder is sufficient and no pumps are required. The vessel was stirred magnetically (coupling of the magnetic stir bar to the stir plate below was confirmed visually prior to starting the experiment) for 30 minutes, after which the stirring was stopped, the water bath heater and agitator, were turned off to minimize vibration, and the vent valve to the vessel was opened slightly so that approximately 1 ml of $CO_2$ gas escaped per minute. The valve was adjusted daily to maintain this rate of $CO_2$ loss. After 1 week, the pressure had entirely escaped. The vessel was opened. Purple diamond-shaped platelet crystals of $Rh_2(O_2C(CF_2)_9F)_4(DMF)_2$ found in the vial were removed and one was analyzed crystallographically. Crystals of complexes 4, and the bis(N,N-dimethylformamide) adduct of complex 2 were obtained and analyzed similarly. Complex 4, although it has fair solubility in cyclohexane and toluene, could still be crystallized by the same method if the volume of toluene was less than or equal to 0.4 mL per 120 mg of the complex. Similar crystallization from $CO_2$-expanded cyclohexane gave a green oil rather than crystals.

B. An alternative method for crystallization of fluorinated complexes. An alternative and sometimes more effective method was to release the $CO_2$ pressure over 1 to 4 hours, after which the vessel would be opened, the vial would be capped tightly, and the vial would be left undisturbed on a shelf for a week. Crystals of complexes $Rh_2(O_2C(CF_2)_9F)_4(MeOH)_2$, $Cr(hexafluoroacetylacetonate)_3$, and tris(3,5-bis(trifluoromethyl)phenyl)phosphine were obtained by this method.

C. Rapid screening of the best conditions for recrystallization. This is performed by placing 13 small glass vials uncapped and upright in a 160 mL reaction vessel. Different proportions of the organic liquid (usually a heavy alkane, cycloalkane or toluene) and the fluorinated solid are placed in each vial, along with a micro stir bar. The recrystallization then proceeds using either of the two methods described above. For particularly volatile solids or solvents, the use of a single vial per vessel is preferred to avoid cross-contamination.

Example 4

A. Loading of a catalyst or catalyst precursor into fluorous silica. Fluorous silica gel was prepared by reacting $RfCH_2CH_2OH$ ($R_f$=poly(hexafluoro-propylene oxide) with $SiCl_4$ (alcohol:$SiCl_4$=2:1) for a week in stirred THF. The HCl off gas was trapped in triethylamine/water. This was done under nitrogen atmosphere to produce $SiCl_2(ORf)_2$. The $SiCl_2(OR_f)_2$ was then reacted under nitrogen with normal silica gel for 5 days to produce the fluorous silica gel. This was then washed repeatedly with water, perfluorohexane, toluene and methanol to remove impurities. Catalyst was deposited onto this fluorous silica gel in the following manner. The fluorous silica gel was added to a solution of a purple fluorinated complex, $Co(O_2CR_f)_2$ (where $R_f$ is a perfluoropolyether tail), in FC-43 (perfluorotributylamine). Over time, the absorbance in the solution decreased significantly, until the solution was clear and the gel purple. The solvent was then removed, leaving behind the catalyst-loaded silica.

B. Extraction of a catalyst from fluorous silica into a $CO_2$-expanded liquid, followed by reabsorption of the catalyst back into the fluorous silica. Catalyst-loaded fluorous silica gel (prepared as in Example 4 A) was placed in a pressure vessel along with liquid methanol. No color was observed in the liquid. Gaseous $CO_2$ was added and coloration of the organic liquid was observed, particularly at 600-800 psi $CO_2$, indicating that the colored complex was being extracted from the fluorous silica by the $CO_2$-expanded methanol. After slow release of the $CO_2$, the complex redeposited on the surface of the fluorous silica.

Example 5

Homogeneous catalysis with catalyst recovery and reuse. Homogeneously-catalyzed hydrogenation of styrene was performed to illustrate the method of catalysis and catalyst recycling using $CO_2$ as a solubility trigger. A microstir bar, the catalyst precursor $[RhCl\{P(C_6H_4\text{-}p\text{-}CH_2CH_2(CF_2)_6F)_3\}_3]$ (10 mg), degassed styrene (0.080 mL, 100:1 mole ratio to catalyst), degassed cyclohexane (to bring the total volume to 0.2 mL), and fluorous silica (45 mg) were added, in that order, to a glass vial under an inert atmosphere. The vial was placed inside a pressure vessel so that it would be held upright. The vessel was allowed to temperature equilibrate in a water bath to 40° C., and was flushed repeatedly with $H_2$. Hydrogen (30 bar) and then $CO_2$ (60 bar) were added. The reaction was allowed to proceed overnight, with stirring. The pressure was then slowly released. The vessel was opened inside an inert gas glove box. Upon opening the vessel in the glovebox, one finds that the catalyst had deposited onto the silica. This is qualitatively observed by the light brown/orange color of the silica (initially the silica powder had been white). The liquid phase was clear in color. To remove the liquid, a syringe and/or a pipet was used in such a manner as to least disrupt the silica phase. This task is made easier if one adds more cyclohexane solvent to remove all the liquid. This was repeated three times, and these "washes" were placed in vials to be analyzed by gas chromatography. Fresh styrene (0.080 mL) and cyclohexane (to bring the total volume to 0.2 mL) were added to the catalyst. The vessel was closed and the cycle repeated.

The hydrogenation of styrene to ethylbenzene was performed in this manner four times, using only the initial batch of Rh catalyst. Chromatographic analysis showed that the hydrogenation was complete after each cycle, demonstrating that the catalyst deactivation or extraction, if any, is not significant enough to adversely affect the yield even after four cycles.

What is claimed is:

1. A method of recrystallizing a fluorinated compound in an organic nonhalogenated solvent, the method comprising:
   applying carbon dioxide gas to the solvent at a pressure effective to enhance the solubility of the fluorinated compound; and
   recrystallizing the fluorinated compound by reducing the pressure of the carbon dioxide gas.

2. The method of claim 1, wherein the pressure of the carbon dioxide gas is about 30-300 bar.

3. The method of claim 1, wherein the organic solvent is pentane, hexane, heptane, octane, nonane, decane, cyclopentane, cyclohexane, dioxane, benzene, toluene, xylene, ether, diisopropylether, ethyl acetate, tetrahydrofuran, triethylamine, tripropylamine, N,N,N',N'-tetramethylethylenediamine, methylene chloride, chloroform, chlorobenzene, acetone, nitrobenzene, acetonitrile, formamide, acetamide, dimethylformamide, dimethylacetamide, nitromethane, methanol, ethanol, propanol, butanol, isopropanol, sec-butanol, tert-butanol, ethylene carbonate, propylene carbonate, glyme, diglyme, dimethylsulfone, or dimethylsulfoxide, or a mixture thereof.

4. The method of claim 1, 2, or 3, wherein the fluorinated compound is a catalyst.

5. The method of claim 4, wherein the catalyst is an organometallic complex of a main group metal, main group semimetal, transition metal, actinide or lanthanide.

6. The method of claim 4, wherein the catalyst comprises highly fluorinated ligands.

7. The method of claim 1, 2, or 3, wherein the pressure is released in about 24 hours or less.

8. The method of claim 7, wherein the pressure is released in about 4 hours or less.

9. The method of claim 1, 2, or 3 further comprising providing a plurality of individual sample containers, each container comprising a fluorinated compound in an organic non-halogenated solvent, the method further comprising:
applying carbon dioxide gas to the solvent in the individual sample containers at a pressure effective to enhance the solubility of the fluorinated compound; and
recrystallizing the fluorinated compounds in the individual sample containers by reducing the pressure of the carbon dioxide gas.

10. The method of claim 9, wherein the method further comprises varying components of the individual samples.

11. The method of claim 9 further comprising screening the recrystallized fluorinated compounds for crystallinity, chemical purity or optical purity.

12. A method of conducting a reaction using a fluorinated compound in an organic solvent, the method comprising applying carbon dioxide gas to an organic solvent comprising a fluorinated compound at a pressure effective to solubilize the fluorinated compound during the reaction.

13. The method of claim 12, wherein the pressure of the carbon dioxide gas is about 40 to 90 bar.

14. The method of claim 12 or 13, wherein the compound is a catalyst.

15. The method of claim 12 or 13, wherein the method comprises:
applying carbon dioxide pressure to a non-halogenated organic solvent comprising at least one substrate and a fluorinated organometallic catalyst, in an effective amount to solubilize the catalyst;
permitting the catalyst to catalyze the reaction of the substrate to form a product; and
reducing the carbon dioxide gaseous pressure, thereby to cause precipitation of the catalyst.

16. The method of claim 15, further comprising recovering the catalyst after the reaction from the solvent.

17. The method of claim 15, wherein carbon dioxide pressure is applied at about 40 to 90 bar.

18. The method of claim 15, wherein the reaction is hydrogenation, hydroboration, hydroformylation, cyclopropanation, C—H insertion reactions, oxidation, hydroxylation, isomerization, coupling reaction, olefin metathesis, polymerization, hydrosilylation, hydrocyanation, epoxidation, or a Diels-Alder reaction.

19. The method of claim 15, wherein the catalyst is an organometallic complex of a main group metal, main group semimetal, transition metal, actinide or lanthanide.

20. The method of claim 12, the method comprising:
applying carbon dioxide pressure to an organic solvent comprising at least one substrate and a fluorinated organometallic catalyst, in an effective amount to solubilize the catalyst;
permitting the catalyst to catalyze the reaction of the substrate to form a product; and reducing the carbon dioxide gaseous pressure, thereby to cause precipitation of the catalyst.

21. The method of claim 12 or 13, further comprising including a fluorinated support material in the organic solvent, wherein the fluorinated support material is capable of adsorbing the catalyst when the carbon dioxide pressure is reduced.

22. The method of claim 21, wherein the fluorinated support material is a fluorinated polymer, or an inorganic or organic support material comprising fluorinated organic groups.

23. The method of claim 21, wherein the method comprises:
applying carbon dioxide pressure to a non-halogenated organic solvent comprising at least one substrate and a fluorinated organometallic catalyst, in an effective amount to solubilize the catalyst;
providing a fluorinated support material in the solvent;
permitting the catalyst to catalyze the reaction of the substrate to form a product; and
reducing the carbon dioxide gaseous pressure, thereby to permit precipitation of the catalyst and adsorption of the fluorinated catalyst on the support material.

24. The method of claim 23, wherein the fluorinated support material is a fluorinated polymer, or an inorganic or organic support material comprising fluorinated organic groups.

25. The method of claim 23, further comprising isolating the support material having the fluorinated catalyst thereon from the solvent.

26. The method of claim 25, further comprising reusing the support material having the fluorinated catalyst thereon to catalyze a second reaction.

27. The method of claim 23, wherein the fluorinated catalyst is adsorbed onto the support material prior to application of the carbon dioxide pressure, and is released from the support material after application of the carbon dioxide pressure.

28. The method of claim 12, wherein the method comprises conducting a plurality of said reactions, wherein individual reactions vary in reaction conditions.

29. The method of claim 28, wherein the plurality of reactions are done in plural different reaction containers;
wherein individual reaction containers comprise an organic solvent, at least one reaction substrate, and a fluorinated organometallic catalyst, and wherein the method comprises:
applying carbon dioxide pressure to the reaction containers in an effective amount to solubilize the catalyst;
permitting the catalyst to catalyze the reaction of the substrate to form a product in the reaction containers; and
reducing the carbon dioxide gaseous pressure, thereby to cause precipitation of the catalyst in the reaction containers.

30. The method of claim 29, wherein the reaction containers are provided within a sealable reaction vessel.

31. The method of claim 29, wherein the amount or identity of at least one of the organic solvent, the reaction substrate, or the catalyst vary in the different reaction containers.

32. The method of claim 31, wherein the method comprises varying the solvent in the different reaction containers.

33. The method of claim 31, wherein the method comprises varying the identity of the catalyst in the different reaction containers.

34. The method of claim 31, wherein the method comprises varying the concentration of the catalyst or reaction substrate in different reaction containers.

35. The method of claim 29, wherein the method further comprises screening the reaction for a reaction product in the individual containers.

36. The method of claim 29, wherein the solvent is a non-halogenated organic solvent.

37. The method of claim 10 further comprising screening the recrystallized fluorinated compounds for crystallinity, chemical purity or optical purity.

38. The method of claim 14, wherein the method comprises:
    applying carbon dioxide pressure to a non-halogenated organic solvent comprising at least one substrate and a fluorinated organometallic catalyst, in an effective amount to solubilize the catalyst;
    permitting the catalyst to catalyze the reaction of the substrate to form a product; and
reducing the carbon dioxide gaseous pressure, thereby to cause precipitation of the catalyst.

39. The method of claim 38, further comprising recovering the catalyst after the reaction from the solvent.

40. The method of claim 38, wherein carbon dioxide pressure is applied at about 40 to 90 bar.

41. The method of claim 38, wherein the reaction is hydrogenation, hydroboration, hydroformylation, cyclopropanation, C—H insertion reactions, oxidation, hydroxylation, isomerization, coupling reaction, olefin metathesis, polymerization, hydrosilylation, hydrocyanation, epoxidation, or a Diels-Alder reaction.

42. The method of claim 38, wherein the catalyst is an organometallic complex of a main group metal, main group semimetal, transition metal, actinide or lanthanide.

43. The method of claim 14, further comprising including a fluorinated support material in the organic solvent, wherein the fluorinated support material is capable of adsorbing the catalyst when the carbon dioxide pressure is reduced.

44. The method of claim 43, wherein the fluorinated support material is a fluorinated polymer, or an inorganic or organic support material comprising fluorinated organic groups.

45. The method of claim 43, wherein the method comprises:
    applying carbon dioxide pressure to a non-halogenated organic solvent comprising at least one substrate and a fluorinated organometallic catalyst, in an effective amount to solubilize the catalyst;
    providing a fluorinated support material in the solvent;
    permitting the catalyst to catalyze the reaction of the substrate to form a product; and
    reducing the carbon dioxide gaseous pressure, thereby to permit precipitation of the catalyst and adsorption of the fluorinated catalyst on the support material.

* * * * *